US009826898B1

United States Patent
Jin et al.

(10) Patent No.: US 9,826,898 B1
(45) Date of Patent: Nov. 28, 2017

(54) COLOR VISION ASSESSMENT FOR DISPLAYS

(71) Applicant: Apple Inc., Cupertino, CA (US)

(72) Inventors: Can Jin, San Jose, CA (US); Nicolas P. Bonnier, Campbell, CA (US); Roy J. E. M. Raymann, Campbell, CA (US); Jiaying Wu, Santa Clara, CA (US)

(73) Assignee: Apple Inc., Cupertino, CA (US)

(*) Notice: Subject to any disclaimer, the term of this patent is extended or adjusted under 35 U.S.C. 154(b) by 0 days.

(21) Appl. No.: 15/362,648

(22) Filed: Nov. 28, 2016

Related U.S. Application Data

(60) Provisional application No. 62/377,454, filed on Aug. 19, 2016.

(51) Int. Cl.
  *A61B 3/02* (2006.01)
  *A61B 3/06* (2006.01)
  *A61B 3/00* (2006.01)

(52) U.S. Cl.
  CPC .......... *A61B 3/066* (2013.01); *A61B 3/0025* (2013.01); *A61B 3/0033* (2013.01); *A61B 3/0041* (2013.01)

(58) Field of Classification Search
  CPC ....... A61B 3/028; A61B 3/0041; A61B 3/032; A61B 3/0091; A61B 6/464; G09G 5/02; G09G 3/2003
  USPC ........ 351/237, 239, 246, 242, 211; 345/589, 345/593, 591, 581
  See application file for complete search history.

(56) References Cited

U.S. PATENT DOCUMENTS

| | | | | |
|---|---|---|---|---|
| 5,589,898 A | * | 12/1996 | Atkinson | ............... A61B 3/066 351/237 |
| 2012/0147163 A1 | | 6/2012 | Kaminsky | |
| 2013/0027420 A1 | | 1/2013 | Felt | |
| 2013/0342555 A1 | | 12/2013 | Braham et al. | |
| 2016/0217723 A1 | | 7/2016 | Kim et al. | |

FOREIGN PATENT DOCUMENTS

EP  2886039  6/2015

OTHER PUBLICATIONS

Mollon et al., "Cambridge Colour Test Handbook", version 1.1, Jan. 2000, 15 pages.

(Continued)

*Primary Examiner* — Hung Dang
(74) *Attorney, Agent, or Firm* — Treyz Law Group, P.C.; Kendall W. Abbasi

(57) ABSTRACT

An electronic device may include a display and control circuitry that operates the display. The control circuitry may be configured to daltonize input images to produce daltonized output images that allow a user with color vision deficiency to see a range of detail that the user would otherwise miss. The daltonization algorithm may be specific to the type and severity of color vision deficiency that the user has. The control circuitry may conduct a color vision assessment using the display. The color vision assessment may include a sequence of test images that are each displayed for a predetermined period of time before moving to the next test image in the sequence. Each test image may include a color patch on a neutral background. A predetermined number of severity levels for each type of color vision deficiency may be tested during the color vision assessment.

20 Claims, 8 Drawing Sheets

(56) References Cited

OTHER PUBLICATIONS

"Test Version of 'Color Blind Check' Android App Available", retrieved from the Internet on Nov. 28, 2016, <URL: http://www.color-blindness.com/2014/06/01/test-version-of-color-blind-check-android-app-aavailable/> Tests (http://www.color-blindness.com/category/tests/), Jun. 1, 2014.

Bonnier et al., U.S. Appl. No. 15/244,940, filed Aug. 23, 2016.

\* cited by examiner

COLOR VISION ASSESSMENT FOR DISPLAYS

This application claims the benefit of provisional patent application No. 62/377,454, filed Aug. 19, 2016, which is hereby incorporated by reference herein in its entirety.

BACKGROUND

This relates generally to displays and, more particularly, to electronic devices with displays.

Electronic devices often include displays. For example, cellular telephones and portable computers often include displays for presenting information to a user.

Some users have a color vision deficiency that makes it difficult to distinguish between different colors on the display. Users with color vision deficiencies may miss a significant amount of visual detail in the images on a display screen, ranging from textual information to photographs and videos.

Daltonization is a process through which colors on a display are adjusted to allow users with color vision deficiencies to distinguish a range of detail they would otherwise miss. Daltonization is sometimes offered by applications such as websites, web browsers, or desktop applications. These applications adjust the display colors in a targeted display area to make the display content in that area more accessible to the user.

To apply the correct daltonization algorithm on a display, the type of color vision deficiency should be determined. However, many people with color vision deficiency do not know what type of color vision deficiency they have or how severe it is. Conventional methods for testing color vision deficiency are either too tedious and time-consuming for users or they are subject to inaccurate results.

It would therefore be desirable to be able to provide displays with improved methods for assessing color vision deficiency.

SUMMARY

An electronic device may include a display and control circuitry that operates the display. The control circuitry may be configured to daltonize input images to produce daltonized output images that allow a user with color vision deficiency to see a range of detail that the user would otherwise miss.

The daltonization algorithm that the control circuitry applies to input images may be specific to the type and severity of color vision deficiency that the user has. The control circuitry may determine the type and severity of color vision deficiency by prompting the user to take a color vision assessment.

The color vision assessment may include a sequence of test images that are each displayed for a predetermined period of time before moving to the next test image in the sequence. Each test image may include a color patch on a different color background. A predetermined number of severity levels for each type of color vision deficiency may be tested during the color vision assessment.

Each test image may include a pattern of tiles with hexagon shapes or other suitable shapes. The tiles may be assigned random luminance values. If the tiles in the test image are located in the background, they may have a first color (e.g., a neutral color such as gray, or other suitable color). If the tiles are located in the color patch region, they may have a test color that is different from the background color. The background color and the test color may be located along a confusion line for a particular type of color vision deficiency. If the user has that particular type of color vision deficiency, he or she may not provide any input to the display. If the user does not have that particular type of color vision deficiency, the user may provide input by selecting the color patch region on the display. Different severity levels may be tested by increasing or decreasing the color difference between the color patch and the background.

DETAILED DESCRIPTION

Figure 1:
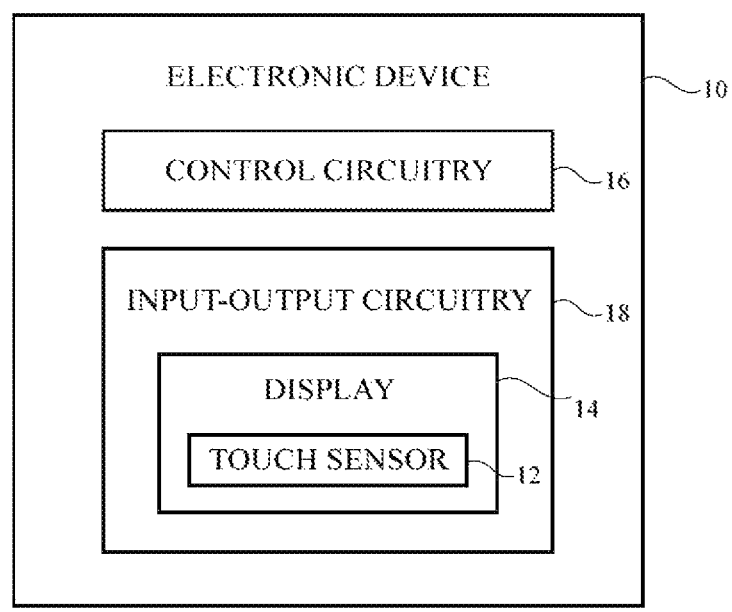
FIG. 1 is a schematic diagram of an illustrative electronic device with a display in accordance with an embodiment.

An illustrative electronic device of the type that may be provided with a display is shown in FIG. 1. Device 10 of FIG. 1 may be a computing device such as a laptop computer, a computer monitor containing an embedded computer, a tablet computer, a cellular telephone, a media player, or other handheld or portable electronic device, a smaller device such as a wrist-watch device (e.g., a watch with a wrist strap), a pendant device, a device embedded in eyeglasses or other equipment worn on a user's head, or other wearable or miniature device, a television, a computer display that does not contain an embedded computer, a gaming device, a navigation device, an embedded system such as a system in which electronic equipment with a display is mounted in a kiosk or automobile, equipment that implements the functionality of two or more of these devices, or other electronic equipment.

As shown in FIG. 1, electronic device 10 may have control circuitry 16. Control circuitry 16 may include storage and processing circuitry for supporting the operation of device 10. The storage and processing circuitry may include storage such as hard disk drive storage, nonvolatile memory (e.g., flash memory or other electrically-programmable-read-only memory configured to form a solid state drive), volatile memory (e.g., static or dynamic random-access-memory), etc. Processing circuitry in control circuitry 16 may be used to control the operation of device 10. The processing circuitry may be based on one or more microprocessors, microcontrollers, digital signal processors, baseband processors, power management units, audio chips, application specific integrated circuits, etc.

Input-output circuitry in device 10 such as input-output devices 18 may be used to allow data to be supplied to device 10 and to allow data to be provided from device 10 to external devices. Input-output devices 18 may include buttons, joysticks, scrolling wheels, touch pads, key pads, keyboards, microphones, speakers, tone generators, vibrators, cameras, sensors, light-emitting diodes and other status indicators, data ports, etc. A user can control the operation of device 10 by supplying commands through input-output devices 18 and may receive status information and other output from device 10 using the output resources of input-output devices 18.

Input-output devices 18 may include one or more displays such as display 14. Display 14 may be a touch screen display that includes a touch sensor 12 for gathering touch input from a user or display 14 may be insensitive to touch. Touch sensor 12 for display 14 may be based on an array of capacitive touch sensor electrodes, acoustic touch sensor structures, resistive touch components, force-based touch sensor structures, a light-based touch sensor, or other suitable touch sensor arrangements. Display 14 and other components in device 10 may include thin-film circuitry.

Control circuitry 16 may be used to run software on device 10 such as operating system code and applications. During operation of device 10, the software running on control circuitry 16 may display images on display 14. Display 14 may be an organic light-emitting diode display, a liquid crystal display, or any other suitable type of display.

Control circuitry 16 may be used to adjust display colors to make the content on display 14 more accessible to users with color vision deficiencies. This may include, for example, daltonizing input images to produce daltonized output images. Daltonization is a process in which the colors in images are adjusted to allow users with color vision deficiencies to observe a range of detail in the images that they would otherwise be unable to see. Control circuitry 16 may transform input images to daltonized output images based on the type of color vision deficiency that a user has. For example, for a user with a missing or malfunctioning M-cone that has trouble distinguishing red from green, control circuitry 16 may daltonize images by rotating green hues towards blue hues and rotating red hues towards yellow hues.

Control circuitry 16 may apply different daltonization algorithms to images depending on the type and severity of color vision deficiency the user has. Control circuitry 16 may determine the type and severity of color deficiency that a user has based on input from the user. For example, a user may manually select his or her specific type of color deficiency from a menu of different types of color deficiencies on display 14. As another example, display 14 may present one or more daltonized images that the user can choose from in order to determine which type of daltonization algorithm works best for the user. If desired, a user may choose to take a color vision deficiency test on device 10 whereby a series of images containing color patches, numbers, letters, or other objects are presented on display 14 and the user provides input to device 10 based on what they observe in the images. One illustrative example of a color vision test is a test that uses Ishihara plates to determine whether a person has a color deficiency, what kind of color deficiency the person has, and how strong the color deficiency is. Other color vision tests may be used, if desired.

Control circuitry 16 may daltonize images using a one-dimensional look-up table (1D LUT), a 1D LUT and a three-by-three matrix, a three-dimensional look-up table (3D LUT), or other suitable color mapping operators. For example, daltonization may be performed using a 3D LUT that is accessed from storage in control circuitry 16. In another suitable embodiment, a 3D LUT or other color mapping operator may be custom built on-the-fly for a user after the user takes a color vision test on device 10. Look-up tables and other color mapping algorithms may be stored in electronic device 10 (e.g., in storage that forms part of control circuitry 16).

After determining the type and severity of color vision deficiency that a user has, control circuitry 16 may daltonize images based on the type and severity of color deficiency (e.g., by mapping input pixel values to daltonized output pixel values using a 3D LUT stored in device 10).

Figure 2:
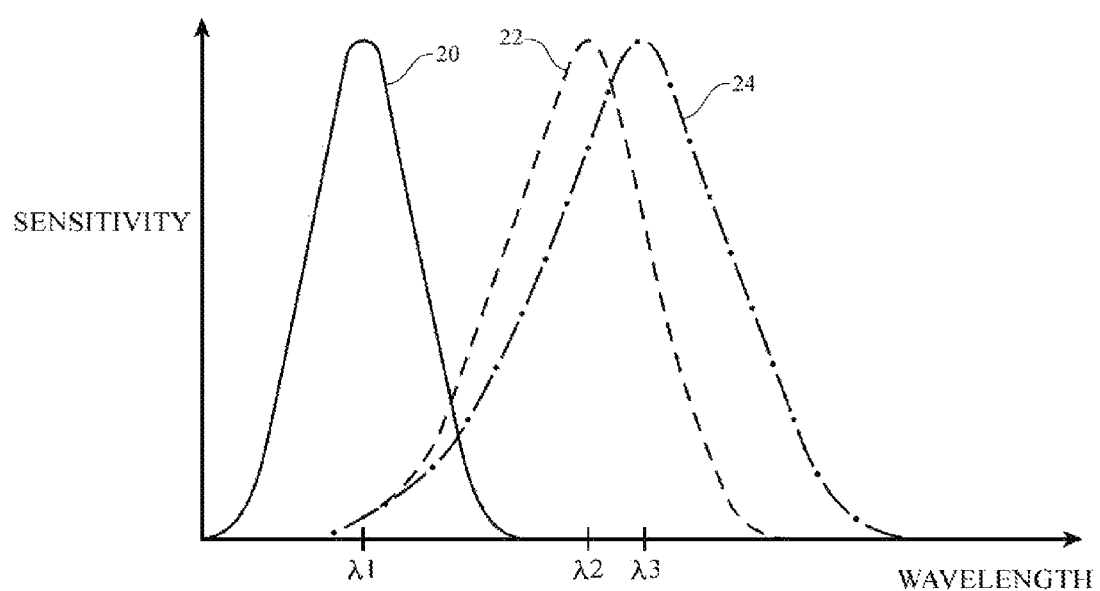
FIG. 2 is a graph illustrating the responsivity spectra of human cone cells with full color perception in accordance with an embodiment.

FIG. 2 is a graph showing the responsivity spectra of human cone cells with full color perception. Curve 20 represents the responsivity of the S-cone (sometimes referred to as the short cone) having a peak sensitivity at $\lambda 1$. Curve 22 represents the responsivity of the M-cone (sometimes referred to as the medium cone) having a peak sensitivity at $\lambda 2$. Curve 24 represents the responsivity of the L-cone (sometimes referred to as the long cone) having a peak sensitivity at $\lambda 3$. Peak wavelength $\lambda 1$ may range between about 420 nm and 440 nm. Peak wavelength $\lambda 2$ may range between about 534 nm and 545 nm. Peak wavelength $\lambda 3$ may range between about 564 nm and 580 nm.

There are various types of color vision deficiency. Monochromatism occurs when an individual only has one or no type of cone. Dichromatism occurs when an individual only has two different cone types and the third type of cone is missing. Types of dichromatism include protanopia in which the L-cone is missing, deuteranopia in which the M-cone is missing, and tritanopia in which the S-cone is missing. Anomalous trichromatism occurs when an individual has all three types of cones but with shifted peaks of sensitivity for one or more cones. Types of anomalous trichromatism include protanomaly in which the peak sensitivity of the L-cone is shifted (e.g., shifted relative to peak wavelength $\lambda 3$ of normal L-cone sensitivity curve 24), deuteranomaly in which the peak sensitivity of the M-cone is shifted (e.g., shifted relative to peak wavelength $\lambda 2$ of normal M-cone sensitivity curve 22), and tritanomaly in which the peak sensitivity of the S-cone is shifted (e.g., shifted relative to peak wavelength $\lambda 1$ of normal S-cone sensitivity curve 20).

The specific type and severity of color vision deficiency can vary significantly from person to person. Even if two individuals have the same type of color vision deficiency (e.g., protanomaly), one may be more severe than the other (e.g., the peak sensitivity of the L-cone for one person may be shifted more relative to peak wavelength $\lambda 3$ of normal L-cone sensitivity curve 24 than that of the other person). Thus, in order to accurately daltonize images for a user, control circuitry 16 must determine the type and severity of color vision deficiency a user has. This helps ensure that images are daltonized with an appropriate daltonization strength so that images are not over-corrected or undercorrected. To determine the type and severity of color vision deficiency a user has, control circuitry 16 may conduct a color vision deficiency assessment using display 14. Control circuitry 16 may then daltonize images with a user-specific daltonization algorithm that is selected based on the results of the color vision deficiency assessment.

Figure 3:
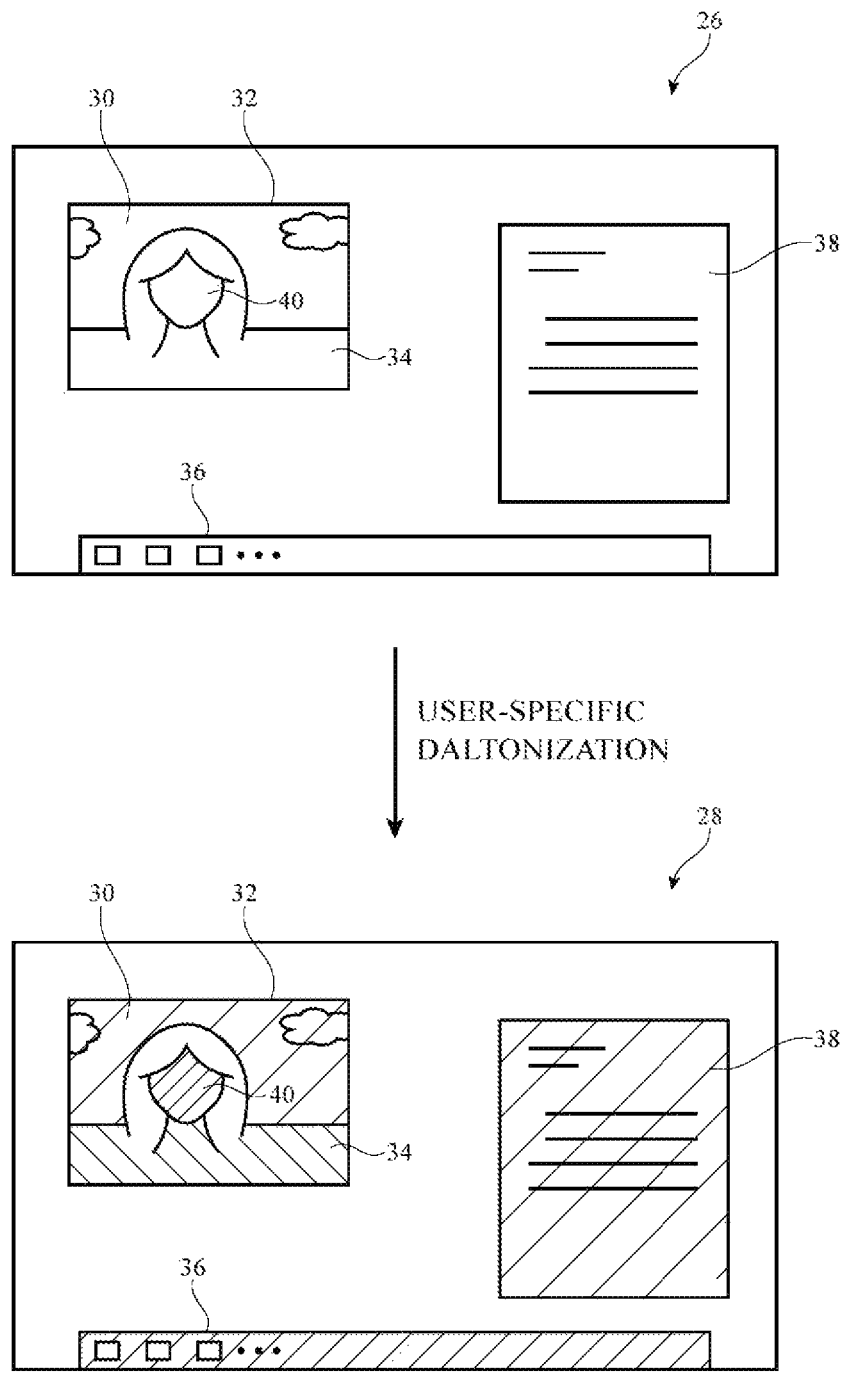
FIG. 3 is a diagram illustrating how a user-specific daltonization algorithm may be applied to an input image to produce a daltonized image in accordance with an embodiment.

FIG. 3 is a diagram illustrating how control circuitry 16 of FIG. 1 uses a user-specific daltonization method. As shown in FIG. 3, original image 26 includes various types of content such as text information 38 (e.g., part of a word processing application, a web browsing application, an e-mail application, etc.), photography 32 (e.g., natural images including common memory colors such as blue sky 30, green grass 34, and skin tones 40), and user interface elements 36 (e.g., icons, virtual buttons, etc.).

Control circuitry 16 may apply a user-specific daltonization algorithm to image 26 to produce daltonized image 28. The daltonization algorithm may be selected based on the type and severity of color vision deficiency that a user has. In daltonized image 28, the user can observe a range of detail that they would not be able to observe in original image 26.

If desired, the daltonization algorithm applied to input image 26 may also be content-specific. For example, daltonized image 28 may have some areas such as text information 38 that have been daltonized more aggressively than other areas such as photograph 32. In other words, the color difference between text information 38 of original image 26 and daltonized image 28 may be greater than the color difference between photograph 32 of original image 26 and daltonized image 28, if desired. For example, blue sky 30, skin tones 40, green grass 34, and other memory colors in original image 26 may be only slightly adjusted or may not be adjusted at all in daltonized image 28, whereas the colors of text area 38 may be sufficiently adjusted to allow important details such as hyperlinks, highlighted text, and other information to become distinguishable to the user. These examples are merely illustrative, however. If desired, memory colors may be daltonized with a relatively high daltonization strength and text information may be daltonized with a relatively low daltonization strength. As another example, different content may be daltonized with similar daltonization strengths but using a different daltonization strategy (e.g., a different daltonization algorithm). In general, daltonization strength may be varied based on content in any suitable fashion.

In order to determine the type and severity of color vision deficiency a user has, control circuitry 16 may use display 14 to display a series of test images for the user. A test image may include a color patch on a neutral (e.g., gray) background. The color patch and the background neutral color may be located along what is referred to as a "confusion line" for a particular type of color vision deficiency. If the user has that type of color vision deficiency, he or she will be unable to distinguish the color patch from the background, or it may take the user a longer period of time to distinguish the color patch than it would a user with full color perception. If the user does not have that type of color vision deficiency, the user may be able to see the color patch and may provide touch input to touch sensor 12 by touching the region of display 14 in which the color patch appears. If desired, user input may be provided using other input devices (e.g., a mouse, a keyboard, a microphone, a camera, etc.). Arrangements in which display 14 is a touch-sensitive display and a user provides input via touch sensor 12 are sometimes described herein as an example.

Figure 4:
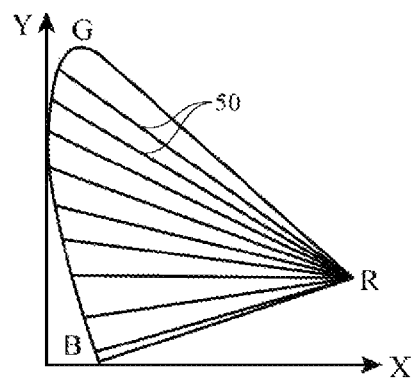
FIG. 4 is a chromaticity diagram showing confusion lines associated with protanopia in accordance with an embodiment.
Figure 5:
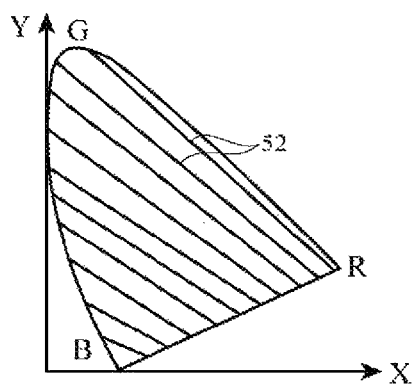
FIG. 5 is a chromaticity diagram showing confusion lines associated with deuteranopia in accordance with an embodiment.
Figure 6:
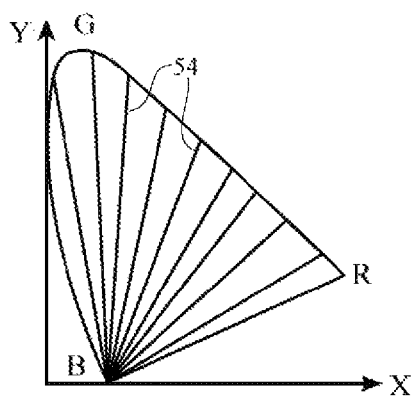
FIG. 6 is a chromaticity diagram showing confusion lines associated with tritanopia in accordance with an embodiment.

FIGS. 4, 5, and 6 are chromaticity diagrams illustrating the confusion lines associated with protanopia, deuteranopia, and tritanopia, respectively. The chromaticity diagrams of FIGS. 4, 5, and 6 each illustrate a two-dimensional projection of a three-dimensional color space and are sometimes referred to as 1931 CIE chromaticity diagrams. A color is represented by chromaticity values x and y on the chromaticity diagram.

A confusion line illustrates which colors a user with color vision deficiency may have difficulty differentiating between. As shown in FIG. 4, confusion lines 50 for protanopia extend between the red and green portions of the color spectrum. This is because users with protanopia have a missing L-cone, making it difficult to distinguish between red and green colors and other colors that lie on one of confusion lines 50.

As shown in FIG. 5, confusion lines 52 for deuteranopia also extend between the red and green portions of the spectrum, but converge at a different point than confusion lines 50 of FIG. 4. This is because users with deuteranopia have a missing M-cone, making it difficult to distinguish red from green but also to distinguish other colors that lie on confusion lines 52 such as purple and greenish blue.

As shown in FIG. 6, confusion lines 54 for tritanopia extend between the green/yellow and blue portions of the color spectrum. This is because users with tritanopia have a missing S-cone, making it difficult to distinguish between blue and green and other colors that lie on one of confusion lines 54.

While the confusion lines of FIGS. 4, 5, and 6 pertain to color vision deficient users with a missing cone, they are also helpful in illustrating which colors may be difficult to distinguish for color-weak users (e.g., users that have three cones but where the peak sensitivity of one cone is shifted relative to the peak sensitivity of the cones of FIG. 2). A user with deuteranomaly, for example, may have an M-cone, but its peak sensitivity is shifted toward the L-cone, making it difficult to distinguish some shades of red from some shades of green.

In order to determine the type and severity of color vision deficiency a user has, control circuitry 16 may use display 14 to conduct a color vision deficiency assessment. During a color vision deficiency assessment, display 14 may display a series of test images one after the other, with each image testing a different type and severity of color vision deficiency.

Figure 7:
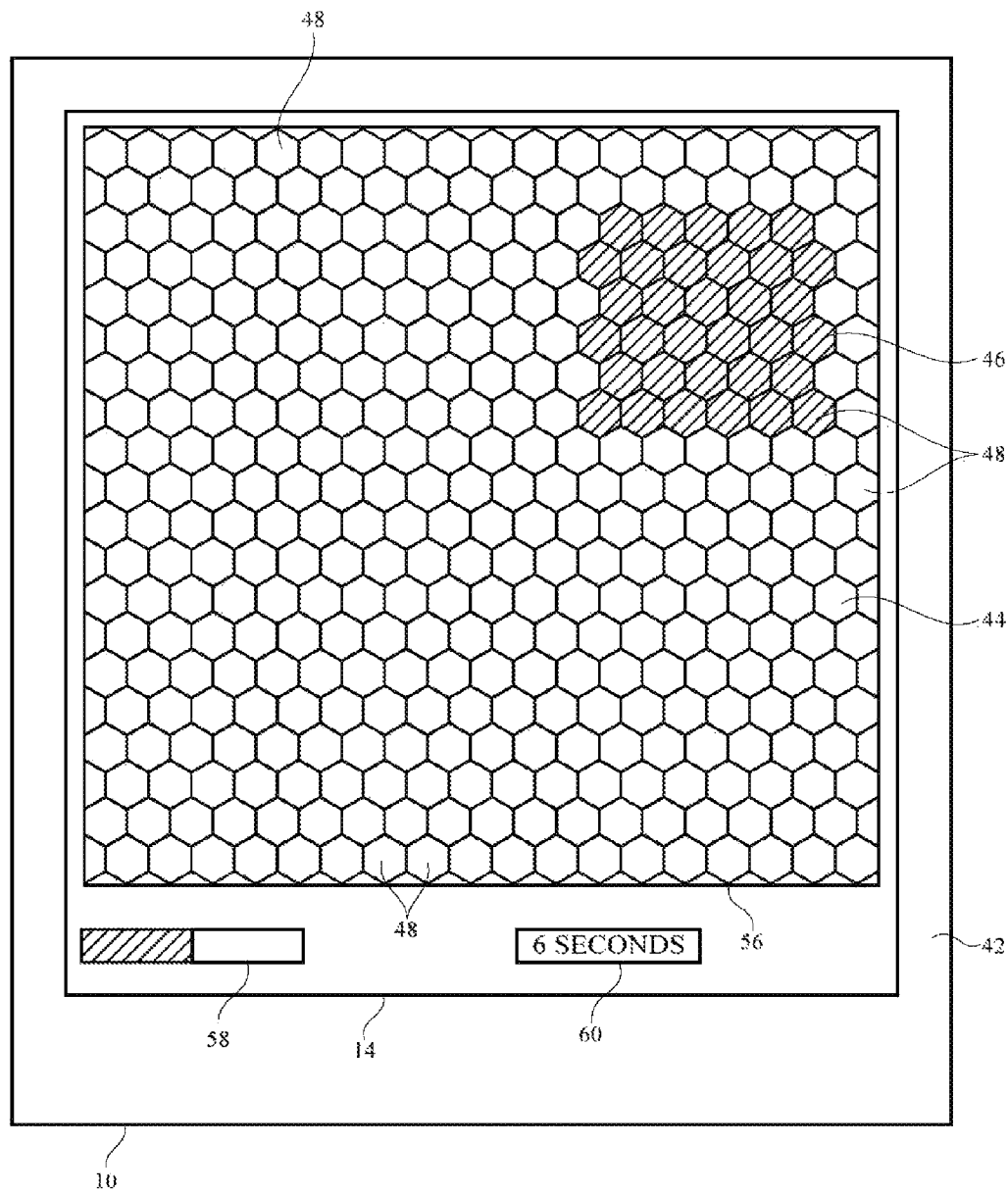
FIG. 7 is a front view of an illustrative electronic device displaying a test image during a color vision deficiency assessment in accordance with an embodiment.

FIG. 7 is a front view of electronic device 10 in which display 14 is displaying an illustrative test image 56 during a color vision deficiency assessment. Test image 56 may include a background such as neutral background 44 and one or more color patches such as color patch 46. Test image 56 may be one of a series of test images that are displayed consecutively, with each test image 56 showing a different color patch 46 in one or more different locations on display 14. If the user is able to distinguish color patch 46 from background 44, the user may provide touch input by touching display 14 where color patch 46 appears. If the user is unable to distinguish (or takes longer to distinguish) color patch 46 from background 44, the user may not provide touch input over color patch 46. Each test image 56 may be displayed until a predetermined time period ends. Test images 56 may be static images that remain on display 14 until the predetermined time period for each image ends, or test images 56 may be moving images that change before the predetermined time period ends. For example, one or more portions of test image 56 may change in luminance or color before switching to the next test image 56, or the location, shape, color, or brightness of color patch 46 on display 14 may change before switching to the next test image, if desired. Arrangements where test images 56 are static test images are sometimes described herein as an example.

Control circuitry 16 may record the user's response or lack of response for each test image 56 in the series, if desired, display 14 may display a box around a region of display 14 in response to a user touching, clicking on, or otherwise selecting that region. If the user did not intend to select that region, the user can cancel the selection by clicking on the box again to de-select. If desired, other types of feedback may be provided to the user to confirm a selection of a region on display 14 (e.g., other types of visual feedback on display 14, audio feedback from a speaker, haptic feedback from a vibrator or other haptic output device, etc.).

In some arrangements, each test image 56 may be displayed for a predetermined (e.g., fixed) period of time before moving to the next test image. In this type of scenario, the user simply selects a region (or makes no selection if no color patch 46 is observed) and waits for the next test image to appear (e.g., after a time period of six seconds, five seconds, or other suitable time period). In other arrangements, display 14 may move to a new test image 56 in response to a user's selection or in response to other input from the user. Arrangements in which each test image 56 is displayed for a fixed period of time are sometimes described herein as an example. Displaying each test image 56 for a predetermined period of time may help minimize any effect that a variance in human response time might have on the results of the test.

In order to determine the type of color vision deficiency a user has, color patch 46 and background 44 may be located on one of confusion lines 50, 52, or 54. In particular, to test for protanopia, the color of patch 46 and the color of background 44 may be located on one of confusion lines 50 of FIG. 4; to test for deuteranopia, the color of patch 46 and the color of background 44 may be located on one of confusion lines 52 of FIG. 5; and to test for tritanopia, the color of patch 46 and the color of background 44 may be located on one of confusion lines 54 of FIG. 6. The color of background 44 may be a neutral color such as gray or may be any other color (e.g., a non-neutral color) located on the same confusion line as color patch 46. Arrangements where background 44 is a neutral color such as gray are sometimes described herein as an example.

If the user is able to distinguish color patch 46 from neutral background 44 in a test image 56 that tests for protanopia, the user may provide touch input to display 14 by touching display 14 on color patch 46, and control circuitry 16 may conclude that the user does not have protanopia. On the other hand, if a user is unable to distinguish color patch 46 from background 44 in a test image 56 that tests deuteranopia (e.g., if the user does not provide the appropriate input), control circuitry 16 may conclude that the user has some type of deuteranopia or deuteranomaly. If desired, control circuitry 16 may test each type of color deficiency a second time if the first test is missed to ensure that the miss was not a mistake. During each color vision deficiency assessment, control circuitry 16 may display different color patches 46 until all three types of color vision deficiency have been tested.

In order to determine the severity of color vision deficiency, each type of color vision deficiency may be tested with more than one test image 56, with each test image 56 for a particular type of color vision deficiency testing a different severity level. The severity level being tested may be based on the color difference between color patch 46 and neutral background 44. In particular, a user that can see a color patch 46 with a significantly different color than background 44 but that cannot see a color patch 46 with a slightly different color than background 44 may have a relatively weak (less severe) color vision deficiency.

Thus, different severity levels for a particular type of color vision deficiency may be tested by showing test images 56 with different color differences between color patch 46 and background 44. For example, to categorize severity into three levels, with level one being the least severe and level three being the most severe, display 14 may display three test images 56 per color vision deficiency type. The test image 56 for level one may have a first color difference between color patch 46 and background 44; the test image 56 for level two may have a second color difference between color patch 46 and background 44, with the second color difference being larger than the first color difference; and the test image 56 for level three may have a third color difference between color patch 46 and background 44, with the third color difference being larger than the first and second color differences. Details regarding the selection of colors for each test image 56 are described in connection with FIG. 10.

If desired, more than three or less than three levels of severity may be tested for each type of color vision deficiency. In general, any suitable number of levels of severity may be tested by increasing or decreasing the number of test images 56 per color vision deficiency type and ensuring that the color difference between color patch 46 and background 44 is adjusted based on the severity level being tested. Arrangements in which three severity levels are tested are sometimes described herein as an example.

Control circuitry 16 may present test images 56 in any suitable order. Test images 56 may, for example, be displayed in a random order to improve reliability. The number of images 56 in each assessment may be determined based on the number of severity levels being tested for each type of color vision deficiency. The number of images 56 may also vary based on the user's response to images 56 during the assessment. If desired, the user may choose the maximum total duration of the test, and control circuitry 16 may select test images 56 accordingly. For example, if a user wishes to take a longer test, control circuitry 16 may test for five levels of severity, whereas if a user wishes to take a shorter test, control circuitry 16 may only test for three levels of severity.

If desired, a countdown timer such as timer 60 may be displayed with each test image 56 so that the user is aware of when display 14 will move to the next test image 56. A progress bar such as progress bar 58 or other visual aid may be displayed to show the user how much of the color vision deficiency assessment has been completed.

The color vision deficiency assessment may include one or more training images (e.g., at the beginning of the test, end of the test, or in between test images 56). A training image may include color patches that are significantly more distinguishable (e.g., significantly more saturated) than color patches 46 of test images 56. The colors on a training image may not be located on any one particular confusion line and should therefore be distinguishable by all users regardless of color vision deficiency type. If a training image does not receive the correct user input, the test may start over, or more training images may be displayed until a correct response is received. Multiple incorrect responses to training images may, if desired, result in control circuitry 16 pausing or stopping the test. If desired, the color vision deficiency assessment may also include blank test images (e.g., images that include background 44 but that do not include any color patches 46).

Prior to displaying any test images 56, training images, or blank test images, device 10 may provide test instructions to the user (e.g., by displaying instructions on display 14, by giving audio instructions to the user via a speaker, etc.). The instructions may describe the test to the user (e.g., may explain how to select or de-select regions, may instruct the user to wait until a new test image appears without providing input if no color patch is perceivable, may explain or show which regions of display 14 the color patches may appear, etc.). By showing the user which regions of display 14 may be used for color patches 46, the user can avoid wasting time "hunting" the entire display area for a color patch.

Test image 56 may be made up of tiles 48. Tiles 48 may have any suitable shape (e.g., hexagon, octagon, or other polygon, square, circle, oval, other suitable shape, or a combination of any two or more of these shapes). Tiles 48 may be located throughout test image 56 (e.g., both background 44 and color patch 46 may be made up of tiles 48). An illustrative pattern for tiles 48 is shown in FIG. 8.

Figure 8:
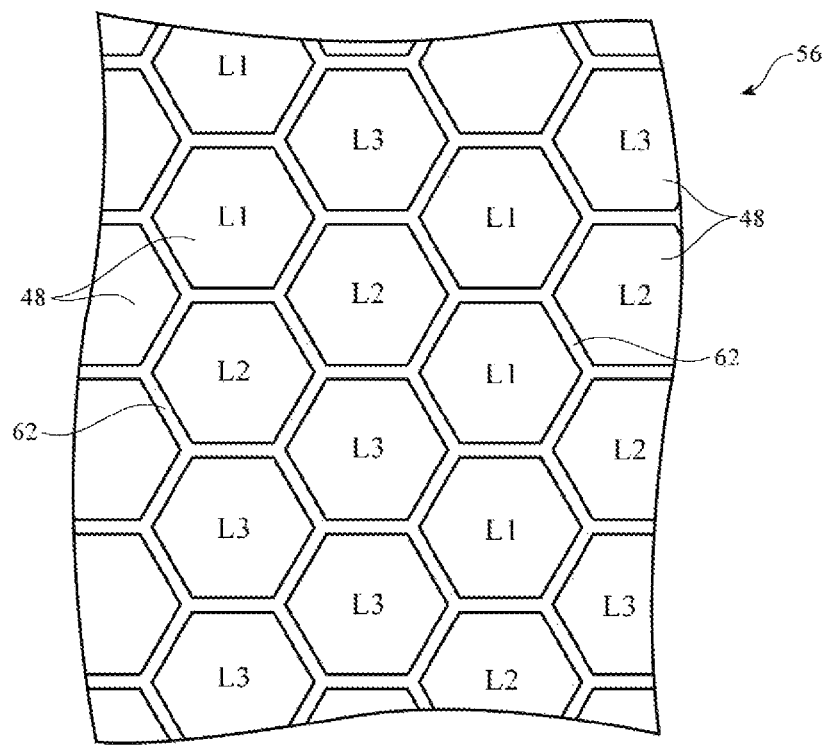
FIG. 8 shows a portion of an illustrative test image that includes hexagon tiles with different luminance levels in accordance with an embodiment.

In the example of FIG. 8, test image 56 is made up of hexagon tiles 48, which are separated from one another by border 62 (sometimes referred to as seam 62). To help "mask" the edges of colored regions 46 against neutral background 44, tiles 48 may have different luminance values. For example, in YUV color space, some tiles 48 may have a luminance (Y) value L, other tiles 48 may have a luminance (Y) value L2, and other tiles 48 may have a luminance (Y) value L3. If desired, more than three or less than three different luminance values may be assigned to tiles 48 of test image 56. The use of three luminance values is sometimes described herein as an example.

The luminance values for tiles 48 in each test image 56 may be randomly assigned or may otherwise be varied across test image 56 so that color patch 46 and background 44 both include tiles 48 of different luminance levels. This type of luminance modulation across image 56 helps ensure that a contrast between the edge of color patch 46 and background 44 does not give away where color patch 46 is located in image 56. Instead, the user can focus on detecting the chromaticity difference between color patch 46 and background 44. The presence of border 62 (e.g., a white or other neutral color border) may also help to avoid contrast detection at the edges of color patch 46.

If desired, the luminance of each tile 48 may stay constant throughout the color vision assessment (e.g., the luminance value of a tile 48 at a given location on display 14 for one test image 56 may be the same as the luminance value of a tile 48 at the same location on display 14 for the next test image 56). This is, however, merely illustrative. If desired, the luminance of each tile 48 may change from one test image 56 to the next test image 56 (while remaining constant during each individual test image 56). In other arrangements, the luminance of one or more tiles 48 may change during the time period for displaying each test image 56. Arrangements in which the luminance for each individual tile 48 remains constant throughout the test are sometimes described herein as an example.

Figure 9:
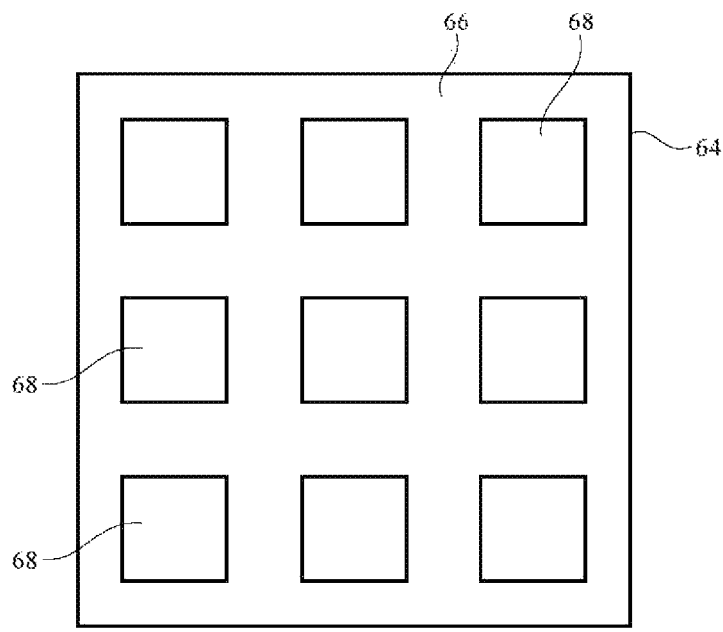
FIG. 9 is a diagram showing how a test color may appear in one or more designated regions of a test image in accordance with an embodiment.

In addition to assigning luminance values (e.g., brightness values) to each tile 48 in test image 56, chromaticity values (e.g., color values) may also be assigned to each tile 48 in test image 56. Mask 64 of FIG. 9 illustrates which areas of each test image 56 may be designated for a possible color patch 46 and which areas of each test image 56 may be designated for background 44. In the example of FIG. 9, mask 64 designates nine possible color patch areas 68, with region 66 between color patch areas 68 designated as background. Thus, tiles 48 that fall in color patch areas 68 will either be assigned chromaticity values corresponding to one of the confusion colors (e.g., if that area 68 is where a color patch 46 is to appear) or be assigned chromaticity values corresponding to a neutral color that blends in with background 44 (e.g., a gray color where red, green, and blue digital input pixel values are equal). Tiles 48 that fall in area 66 will form part of background 44 and will therefore be assigned chromaticity values corresponding to a neutral color (e.g., a gray color where red, green, and blue digital input pixel values are equal).

If desired, test images 56 may each include only one color patch 46 for testing one type of color vision deficiency or test images 56 may each include more than one color patch 46 for testing two different types and/or two different severity levels of color vision deficiency. The position of color patch 46 on display 14 may change randomly from test image to test image.

The use of nine designated regions for color patches 46 is merely illustrative. If desired, there may be greater or fewer than nine designated regions for color patches 46. Color patches 46 need not be rectangular as shown in the example of FIG. 7. Color patches 46 may be circle, oval, zigzag, serpentine, stripes, or any other suitable shape or pattern.

The luminance and chromaticity values for tiles 48 of each test image 56 may be determined by control circuitry 16 in device 10 or may be determined by a separate processor. For example, during manufacturing of device 10, a processor may determine luminance and chromaticity values for each test image 56 in the color vision assessment and may produce corresponding color vision assessment display data. The color vision assessment display data may be loaded on device 10 and stored in control circuitry 16. When it is desired to conduct a color vision assessment with device 10, control circuitry 16 may conduct the assessment using the stored color vision assessment data.

Luminance and chromaticity values for each tile 48 may be determined in YUV color space or in any other suitable color space. In arrangements where luminance and chromaticity values are determined in YUV color space, each tile 48 may be assigned a random luminance (Y) value (e.g., L1, L2, or L3 of FIG. 8) regardless of whether that tile 48 is in one of color patch areas 68 or in background area 66. Each tile 48 may also be assigned chromaticity coordinates (u', v') depending on whether that tile 48 is in one of color patch areas 68 or background area 66. The YUV information for each tile 48 is then converted into the color space needed for display 14 (e.g., sRGB or other suitable color space).

Figure 10:
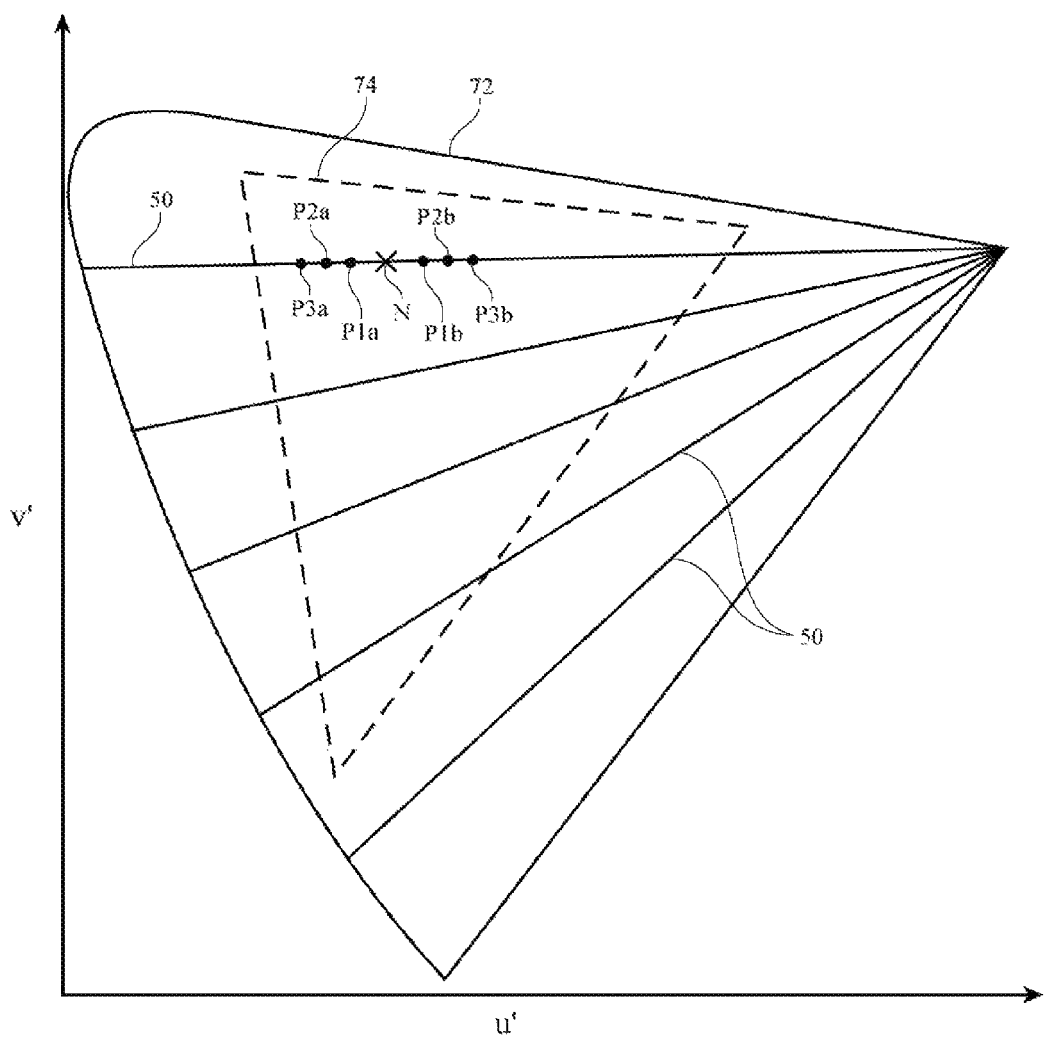
FIG. 10 is a chromaticity diagram illustrating how test colors may be selected for each type of color vision deficiency in accordance with an embodiment.

FIG. 10 is a u'v' chromaticity diagram showing how chromaticity values for each color patch 46 may be determined. Bounded region 72 represents a two-dimensional projection of the entire visible spectrum, whereas bounded region 74 represents a two-dimensional projection of the available color space for a display such as display 14. In the example of FIG. 10, confusion lines 50 for protanopia and protanomaly are shown. As described in connection with FIG. 7, the color of background 44 and the color of color patch 46 in each test image 56 may be located along the same confusion line for a particular type of color vision deficiency. Thus, for protanopia and protanomaly, the colors for each test image 56 may be located along one of confusion lines 50 of FIG. 10.

Point N of FIG. 10 represents a neutral (e.g., gray) color on confusion line 50, whereas points P1$a$, P1$b$, P2$a$, P2$b$, P3$a$, and P3$b$ represent non-neutral colors on confusion line 50. A neutral color on a display refers to the color produced when the digital input pixel values for all of the subpixels in a pixel are equal (e.g., when red, green, and blue subpixels in a pixel receive the same digital input pixel value). A non-neutral color on a display refers to a color produced when the digital input pixel values for the subpixels in a pixel are not equal (e.g., when red, green, and blue subpixels in a pixel receive different digital input pixel values).

Each of points P1a, P1b, P2a, P2b, P3a, and P3b represents a color to be used for color patch 46 in a test image 56 that is testing for protanopia or protanomaly. Neutral color N represents the color of background 44 for each test image 56 that is testing for protanopia or protanomaly. The severity level being tested with a given color depends on the distance between that color and neutral color N (e.g., the distance on a u'v' chromaticity diagram). In the example of FIG. 10, colors at points P1a and P1b are the closest to neutral color N and may therefore be used to test the lowest severity level. Colors at points P2a and P2b are the second closest to neutral color N and may be used to test the second lowest severity level. Colors at points P3a and P3b are the furthest from neutral color N and may be used to test the highest severity level.

In the example of FIG. 10, each severity level is tested using two colors (e.g., P1a and P1b), one from each side of neutral color N on line 50 and both equidistant to neutral color N. This is, however, merely illustrative. If desired, each severity level may be tested with only one color or may be tested with more than two colors (e.g., by selecting a neutral color and one or more non-neutral colors from a different confusion line 50).

To avoid false positives in the color vision assessment, the minimum distance between the lowest severity level (P1a and P1b) and the neutral color (N) should correspond to a color difference that is greater than (or equal to, if desired), a just-noticeable-difference (JND) threshold.

The test images 56 for protanopia/protanomaly may therefore include neutral color N in background 44 and test colors P1a, P1b, P2a, P2b, P3a, and P3b in color patches 46. If each color is tested in a different test image 56, then the protanopia/protanomaly portion of the test may include six different images (one for each of P1a, P1b, P2a, P2b, P3a, and P3b). A similar color selection may be done for the deuteranopia/deuteranomaly portion of the test and for the tritanopia/tritanomaly portion of the test, resulting in a total of eighteen different images. This is, however, merely illustrative. The number of test images 56 may change depending on the number of severity levels tested and the number of colors tested at a given severity level. If desired, the number of test images 56 presented in a given assessment displayed may also change based on how a user responds to images 56 in that assessment. For example, if a user misses P1a, control circuitry 16 may test P1a again with an additional test image 56 to ensure that the miss was not a mistake.

If desired, a staircase approach may be used to determine the severity of color vision deficiency. In this type of arrangement, the severity is determined by starting at a very high color difference from neutral color N and subsequently testing color after color, reducing the color difference with each test until the threshold is found (e.g., until a user misses the color). With the staircase method, the number of severity levels tested varies depending on where the threshold is found. With the method of FIG. 10, a predetermined number of severity levels are tested and the severity is determined based on the predetermined severity levels.

Figure 11:
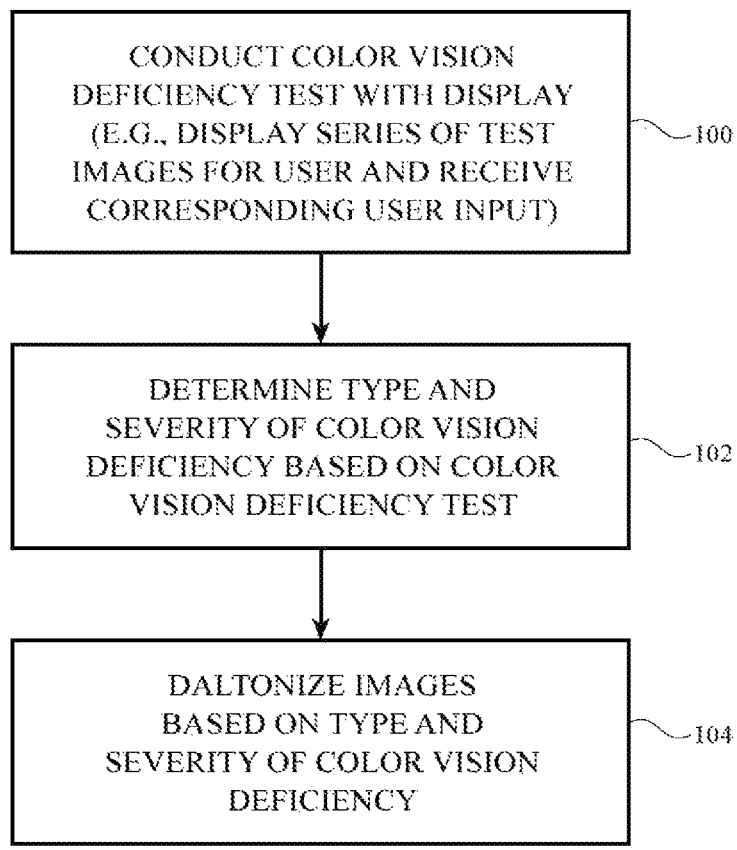
FIG. 11 is a flow chart of illustrative steps involved in daltonizing images based on the type and severity of a user's color vision deficiency in accordance with an embodiment.

FIG. 11 is a flow chart of illustrative steps involved in displaying daltonized images for a user with a daltonization algorithm that is specific to the user's type and severity of color vision deficiency.

At step 100, control circuitry 16 may use display 14 to conduct a color vision deficiency assessment. This may include, for example, displaying a series of test images such as test image 56 of FIG. 7. Each test image may include color patch 46 on neutral background 44. The location of color patch 46 on display 14 may change from one image 56 to the next image 56. Each test image 56 may be displayed for a certain period of time (e.g., five seconds, six seconds, seven seconds, or other suitable period of time). If the user is able to distinguish color patch 46 from background 44, the user may select the color patch 46 by tapping color patch 46 (e.g., providing touch input to touch sensor 12) or by otherwise indicating a selection of that area of display 14. If the user is unable to distinguish color patch 46 from background 44, the user may not provide any input to display 14. Control circuitry 16 may record the user's response or lack of response to each test image 56 until all types and severity levels have been tested. If a user misses a color in a test image 56, control circuitry 16 may add a second test image 56 to test this color again to ensure that the first miss was not a mistake.

At step 102, control circuitry 16 may determine the type and severity of color vision deficiency based on the results of the color vision assessment conducted in step 100. For example, control circuitry 16 may compare the user's response to protanopia colors, deuteranopia colors, and tritanopia colors. If any of the test colors were missed twice by a user, control circuitry 16 may determine the type of color vision deficiency based on which of these missed test colors had the highest severity level. If a tie exists between two types of color vision deficiency, control circuitry 16 may determine type based on which type has a higher prevalence in the population (e.g., if there is a tie between protanomaly and deuteranomaly, deuteranomaly may be selected because deuteranomaly is more prevalent in the human population). Control circuitry 16 may determine the severity level based on which colors were missed for the particular type of color vision deficiency. For example, if a user misses P2a and P2b (FIG. 10), control circuitry 16 may conclude that the user has protanomaly, with a relative severity of 0.66 (level 2 out of 3 levels, or 0.66). As another example, if a user misses P2a, P2b, and P3a, but is able to identify P3b, the severity level may be averaged between 2 and 3 (e.g., for a relative severity of 0.83).

At step 104, control circuitry 16 may select a daltonization algorithm based on the type and severity of color vision deficiency determined in step 102 and may daltonize input images (e.g., input image 26 of FIG. 3) to produce daltonized output images (e.g., daltonized image 28 of FIG. 3) with the selected daltonization algorithm. Display 14 may display the daltonized images so that the user can see details in the image that he or she would otherwise miss.

The foregoing is merely illustrative and various modifications can be made by those skilled in the art without departing from the scope and spirit of the described embodiments. The foregoing embodiments may be implemented individually or in any combination.

What is claimed is:

1. An electronic device, comprising:
 a display that displays a sequence of test images during a color vision assessment, wherein each test image comprises a color patch on a background, wherein the display displays each test image in the sequence for a predetermined period of time, and wherein the display comprises a touch sensor that receives input from a user during the color vision assessment; and control circuitry that determines a type and severity of color vision deficiency that the user has based on the input.

2. The electronic device defined in claim 1 wherein each test image comprises a pattern of tiles.

3. The electronic device defined in claim 2 wherein the tiles in each test image comprise hexagon tiles.

4. The electronic device defined in claim 3 wherein the tiles in each test image are separated from one another by white borders.

5. The electronic device defined in claim 2 wherein the tiles in each test image are each randomly assigned one of a plurality of luminance values and wherein the luminance value for each tile remains constant during the predetermined period of time that the test image is displayed.

6. The electronic device defined in claim 1 wherein a position of the color patch on the background changes throughout the sequence of test images.

7. The electronic device defined in claim 1 wherein a color of the color patch on the background changes throughout the sequence of test images.

8. The electronic device defined in claim 1 wherein the color patch is a first color, wherein the background is a second color, and wherein the first and second colors are located on a confusion line associated with a particular type of color vision deficiency.

9. The electronic device defined in claim 1 wherein the sequence of test images comprises test images that test for protanomaly, test images that test for deuteranomaly, and test images that test for tritanomaly.

10. The electronic device defined in claim 9 wherein the test images that test for protanomaly comprise at least first, second, and third test images for testing three different severity levels of protanomaly, wherein the test images that test for deuteranomaly comprise at least first, second, and third test images for testing three different severity levels of deuteranomaly, and wherein the test images that test for tritanomaly comprise at least first, second, and third test images for testing three different severity levels of tritanomaly.

11. A method for conducting a color vision assessment with an electronic device having a display, a touch sensor, and control circuitry, comprising:

with the display, displaying at least first, second, and third test images for equal periods of time, wherein the first test image comprises a first test color on first background color, the second test image comprises a second test color on a second background color, and the third test image comprises a third test color on a third background color;

with the touch sensor on the display, receiving input from a user on at least one of the first, second, and third test images; and with the control circuitry, determining a type and severity of color vision deficiency that the user has based on the input from the user.

12. The method defined in claim 11 wherein each of the first, second, and third test images comprises a pattern of tiles with different luminance values.

13. The method defined in claim 11 wherein a location of the first test color on the display is different from a location of the second test color on the display.

14. The method defined in claim 11 wherein the first test image tests for protanomaly, the second test image tests for deuteranomaly, and the third test image tests for tritanomaly.

15. The method defined in claim 14 wherein the first test color and the first background color are located on a confusion line associated with protanomaly, wherein the second test color and the second background color are located on a confusion line associated with deuteranomaly, and the third test color and the third background color are located on a confusion line associated with tritanomaly.

16. A method for operating an electronic device to display daltonized images for a user, wherein the electronic device comprises a display, control circuitry, and an input device, comprising:

with the display, displaying a sequence of test images for the user during a color vision assessment, wherein each test image in the sequence tests one of three different color vision deficiency types and one of a plurality of predetermined severity levels;

with the input device, receiving input from the user during the color vision assessment; and with the control circuitry, determining a type and severity of color vision deficiency that the user has based on the input; and with the control circuitry, daltonizing input image data to produce daltonized image data based on the type and severity of color vision deficiency that the user has.

17. The method defined in claim 16 wherein displaying the sequence of test images comprises displaying the sequence of test images until all three types of color vision deficiency have been tested and until all severity levels in the plurality of predetermined severity levels have been tested.

18. The method defined in claim 16 wherein displaying the sequence of test images for the user comprises displaying each test image for a predetermined period of time.

19. The method defined in claim 18 wherein each test image is static for the predetermined period of time.

20. The method defined in claim 16 wherein the input device comprises a touch sensor and wherein receiving input from the user comprises receiving touch input on a color patch in at least one of the test images.

* * * * *